US010080691B2

(12) United States Patent
Nair et al.

(10) Patent No.: US 10,080,691 B2
(45) Date of Patent: Sep. 25, 2018

(54) ABSORBENT PRODUCT CONTAINING ABSORBENT ARTICLES EACH HAVING DIFFERENT GRAPHIC

(71) Applicant: The Procter & Gamble Company, Cincinnati, OH (US)

(72) Inventors: Radhakrishnan Janardanan Nair, Cincinnati, OH (US); Kesyin Fugger Hsueh, Cincinnati, OH (US); Michael Vincent Gray, Cincinnati, OH (US); Jay Tao, Ashiya Hyogo (JP); Kazuyuki Ohnishi, Takaishi Osaka (JP); Limin Song, Cincinnati, OH (US); Michael Irwin Lawson, Fairfield, OH (US); Matthew Gerald McNally, West Chester, OH (US); Deborah Kay Kokoruda, Terrace Park, OH (US); George Bartol Glackin, III, Wyoming, OH (US); Koichi Tomi, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 907 days.

(21) Appl. No.: 14/552,579

(22) Filed: Nov. 25, 2014

(65) Prior Publication Data

US 2015/0082751 A1 Mar. 26, 2015

Related U.S. Application Data

(60) Continuation of application No. 13/850,431, filed on Mar. 26, 2013, now abandoned, which is a division of
(Continued)

(51) Int. Cl.
*A61F 13/15* (2006.01)
*A61F 13/20* (2006.01)
(Continued)

(52) U.S. Cl.
CPC .. *A61F 13/15585* (2013.01); *A61F 13/51496* (2013.01); *A61F 13/5511* (2013.01);
(Continued)

(58) Field of Classification Search
CPC .......... A61F 13/15585; A61F 13/51496; A61F 13/55145; A61F 2013/8497
See application file for complete search history.

(56) References Cited

U.S. PATENT DOCUMENTS

| 3,998,446 A | 10/1976 | Dent |
| 4,393,386 A | 7/1983 | Di Giulio |

(Continued)

FOREIGN PATENT DOCUMENTS

| CH | 609277 | 2/1979 |
| DE | 199208582 U1 | 11/1992 |

(Continued)

OTHER PUBLICATIONS

International Search Report for PCT/US2004/001429, dated Jul. 26, 2004.

*Primary Examiner* — Michele M Kidwell
(74) *Attorney, Agent, or Firm* — George H. Leal; Andrew J. Hagerty

(57) ABSTRACT

In one aspect, an absorbent product includes a package and at least n absorbent articles contained in the package (n is greater than 10). Each of the absorbent articles has a body contacting surface and a garment contacting surface. Each of the absorbent articles includes a component material disposed between the body contacting surface and the garment contacting surface. The component material has a printed graphic which is seen through either the body contacting or garment contacting surfaces. The n graphics of the n absorbent articles are different from each other, and preferably have a predetermined association. In another aspect, a
(Continued)

method is directed to printing a graphic on a sheet material which will become a component material for the absorbent articles. In another aspect, a method is directed to producing the absorbent product including the package and the n absorbent articles contained in the package.

11 Claims, 6 Drawing Sheets

Related U.S. Application Data application No. 10/751,362, filed on Jan. 5, 2004, now abandoned.

(60) Provisional application No. 60/441,432, filed on Jan. 21, 2003.

(51) Int. Cl.
| | |
|---|---|
| *A61F 13/551* | (2006.01) |
| *B41J 3/407* | (2006.01) |
| *B65D 75/52* | (2006.01) |
| *B41M 5/00* | (2006.01) |
| *B65B 5/10* | (2006.01) |
| *A61F 13/514* | (2006.01) |
| *A61F 13/84* | (2006.01) |
| *B65D 85/07* | (2017.01) |

(52) U.S. Cl.
CPC ......... *A61F 13/55145* (2013.01); *B41J 3/407* (2013.01); *B41M 5/0047* (2013.01); *B65B 5/10* (2013.01); *B65D 75/522* (2013.01); *A61F 2013/8497* (2013.01); *B65D 85/07* (2018.01)

(56) References Cited

U.S. PATENT DOCUMENTS

| | | | |
|---|---|---|---|
| 4,444,103 A | 4/1984 | Cronin | |
| 4,535,694 A | 8/1985 | Fukada | |
| 4,695,278 A | 9/1987 | Lawson | |
| 4,735,663 A | 4/1988 | Hasegawa | |
| 4,753,649 A | 6/1988 | Pazdernik | |
| 4,795,454 A | 1/1989 | Dragoo | |
| 4,837,715 A | 6/1989 | Ungpiyakul et al. | |
| 4,884,504 A | 12/1989 | Sillars | |
| 4,893,559 A | 1/1990 | Sillars | |
| 4,896,600 A | 1/1990 | Rogge et al. | |
| 5,000,725 A | 3/1991 | Bauknecht | |
| 5,009,157 A | 4/1991 | Rogge et al. | |
| 5,125,339 A | 6/1992 | Rogge | |
| 5,127,746 A | 7/1992 | Rogge | |
| 5,174,207 A | 12/1992 | Wallmann et al. | |
| 5,184,551 A | 2/1993 | Wallmann et al. | |
| 5,235,515 A | 8/1993 | Ungpiyakul et al. | |
| 5,286,543 A | 2/1994 | Ungpiyaku et al. | |
| 5,299,479 A | 4/1994 | Wallmann et al. | |
| 5,373,788 A | 12/1994 | Schoen | |
| 5,458,062 A | 10/1995 | Goldberg et al. | |
| 5,458,590 A | 10/1995 | Schleinz et al. | |
| 5,470,300 A | 11/1995 | Terranova | |
| 5,503,076 A | 4/1996 | Yeo | |
| 5,607,145 A | 3/1997 | Lovell | |
| 5,695,855 A | 12/1997 | Yeo et al. | |
| 5,735,210 A | 4/1998 | Rogge et al. | |
| 5,795,280 A | 8/1998 | Fowler et al. | |
| 5,818,719 A | 10/1998 | Brandon et al. | |
| 5,897,541 A | 4/1999 | Uitenbroek et al. | |
| 5,927,199 A | 7/1999 | Achelpohl et al. | |
| 5,967,665 A | 10/1999 | MacDonald et al. | |
| 5,980,087 A | 11/1999 | Brandon et al. | |
| 6,035,781 A | 3/2000 | Rogge et al. | |
| 6,037,959 A | 3/2000 | Fassler et al. | |
| 6,273,313 B1 | 8/2001 | Noll et al. | |
| 6,352,528 B1 | 3/2002 | Weber et al. | |
| 6,354,984 B1 | 3/2002 | Hensley et al. | |
| 6,454,095 B1 | 9/2002 | Brisebois et al. | |
| 6,558,499 B1 | 5/2003 | Pargass et al. | |
| 6,572,575 B1 | 6/2003 | Shimada et al. | |
| 6,719,742 B1 | 4/2004 | McCormack et al. | |
| 6,723,080 B1 | 4/2004 | Habib et al. | |
| 6,923,321 B2 | 8/2005 | Samolinski et al. | |
| 6,957,884 B2 | 10/2005 | Sharma et al. | |
| 7,014,637 B1 | 3/2006 | Denti et al. | |
| 7,172,667 B2 | 2/2007 | Vergona | |
| 7,178,571 B2 | 2/2007 | Vergona | |
| 7,185,761 B2 | 3/2007 | Molina et al. | |
| 7,340,417 B2 | 3/2008 | Kaufman et al. | |
| 7,896,858 B2 | 3/2011 | Trennepohl et al. | |
| 2002/0097259 A1 | 7/2002 | Marshall et al. | |
| 2002/0147749 A1 | 10/2002 | Briseboi et al. | |
| 2002/0152001 A1 | 10/2002 | Knipp et al. | |
| 2003/0105443 A1* | 6/2003 | Ohnishi | A61F 13/15772 604/370 |
| 2003/0126028 A1 | 7/2003 | Kaufman et al. | |
| 2004/0143231 A1 | 7/2004 | Nair et al. | |
| 2005/0116976 A1 | 6/2005 | Salacz et al. | |
| 2005/0149389 A1 | 7/2005 | Odorzynski | |
| 2005/0186416 A1 | 8/2005 | Sebastian et al. | |
| 2005/0217791 A1 | 10/2005 | Costello et al. | |
| 2006/0020249 A1 | 1/2006 | Allen | |
| 2006/0129115 A1 | 6/2006 | Visscher et al. | |
| 2006/0135927 A1 | 6/2006 | Zander et al. | |
| 2006/0167430 A1 | 7/2006 | Denit et al. | |
| 2006/0247594 A1 | 11/2006 | Nickel et al. | |
| 2007/0239126 A1 | 10/2007 | Wilson et al. | |
| 2008/0059324 A1 | 3/2008 | Bakken et al. | |
| 2008/0077415 A1 | 3/2008 | Shannon et al. | |
| 2008/0082071 A1 | 4/2008 | Bryant et al. | |
| 2008/0097875 A1 | 4/2008 | Kaufman et al. | |
| 2013/0219830 A1 | 8/2013 | Nair et al. | |

FOREIGN PATENT DOCUMENTS

| | | |
|---|---|---|
| DE | 199208583 U1 | 12/1992 |
| DE | 199211483 U1 | 1/1993 |
| DE | 10311514 | 10/2004 |
| EP | 0 018 147 A1 | 10/1980 |
| EP | 0 029 312 A1 | 5/1981 |
| EP | 1 704 842 A1 | 9/2006 |
| EP | 1 884 360 A2 | 2/2008 |
| JP | 58-71173 | 4/1983 |
| JP | 05317357 | 3/1993 |
| JP | 10244656 | 9/1998 |
| JP | 11129595 | 5/1999 |
| JP | 11129596 | 5/1999 |
| JP | 2000000266 | 1/2000 |
| JP | 2002191637 | 7/2002 |
| JP | 2002248128 | 9/2002 |
| JP | 2002369841 | 12/2002 |
| JP | 2003300655 | 10/2003 |
| JP | 2004000648 | 1/2004 |
| JP | 2004160929 | 6/2004 |
| JP | 2005205798 | 8/2005 |
| JP | 2005273108 | 10/2005 |
| JP | 2005297461 | 10/2005 |
| NL | 7810516 | 4/1980 |
| WO | WO 91/08110 A1 | 6/1991 |
| WO | WO 99/32164 | 7/1999 |
| WO | WO 99/047752 | 9/1999 |
| WO | WO 99/60973 | 12/1999 |
| WO | WO 00/13632 | 3/2000 |
| WO | WO 00/76442 | 12/2000 |
| WO | WO 01/21126 | 3/2001 |
| WO | WO 02/096331 | 12/2002 |

\* cited by examiner

ABSORBENT PRODUCT CONTAINING ABSORBENT ARTICLES EACH HAVING DIFFERENT GRAPHIC

FIELD OF THE INVENTION

The present invention relates to absorbent articles. More particularly, the present invention relates to an absorbent product which contains absorbent articles each having a different graphic.

BACKGROUND

Infants and other incontinent individuals wear a disposable article such as a disposable diaper to receive and contain urine and other body exudates. Absorbent articles function to contain the discharged materials and to isolate these materials from the body of the wearer and from the wearer's garments and bed clothing. It is generally known in the art that disposable absorbent articles have many different basic designs. Examples of such disposable articles include disposable diapers (for baby and adult) including pull-on diapers and training pants, disposable absorbent pads including sanitary napkins, pantiliners and incontinent pads, disposable underwears, and disposable panties for menstrual use.

The exterior of these disposable absorbent articles is covered with a flexible, liquid impervious member to prevent a leakage of absorbed liquids from the disposable absorbent articles. Such a liquid impervious member is generally referred to as a backsheet, and is often constructed from a liquid impervious material such as a polyethylene film, and other outer cover material such as a nonwoven material (if desired). The backsheet constitutes the garment contacting surface of the absorbent articles.

It is also known that the garment contacting surface of the absorbent articles often has a printed graphic(s) to get users' or consumers' positive attention not only in use but also in the market. Such a graphic(s) is typically printed on either a landing zone material or a backsheet material. (The landing zone material is the anchor zone member for the tape fastening system in a tape type diaper.) Printing these graphics on the garment contacting surface of disposable absorbent articles has been becoming popular among consumers due to their entertainment functions.

Those graphics are typically printed by using conventional printing techniques such as the gravure and flexography technologies which employ a printing plate to print the graphic on a sheet material (e.g., a backsheet material, a landing zone material, and a fastening tape material). The printing plate has ink images for graphics to be printed. The printing plate is typically mounted on a printing cylinder in a printing process. In the printing process, when the cylinder rotates, the printing plate contacts the sheet material to transfer the ink images to the sheet material thereby printing the graphics thereon.

The number of the ink images which can be prepared in the printing plate depends on the sizes of the ink images (or the graphics to be printed), the printing plate and the cylinder. In general, since the size of the landing zone member is not large, the size of the ink images prepared in the printing plate tends to be small. On the other hand, since the size of the backsheet is relatively large (i.e., clearly larger than the landing zone member), the size of the repeated ink images tends to be large. This means that the total area of the printing plate is occupied by a small number of ink images. As a result, the number of the graphics to be printed is limited in particular for a relatively large component material of disposable absorbent articles such as a backsheet material.

Because of the above reasons, the variety of the graphics printed on conventional disposable absorbent articles is limited in one package. For example, the maximum number in the variety of the graphics printed on conventional disposable absorbent articles which are packed in one package is 10.

Thus, it is understood that this limitation results in preventing users or consumers from enjoying more variety of graphics in the disposable absorbent articles packed or contained in one package. In addition, this limitation also limits the function of the graphics within a limited area, i.e., a mere entertainment for enjoying the variety within the limited number. Further, this limitation has become a restriction to illustrate a complete theme which is believed to help children's education or development.

Hence, there is a need for an absorbent product that can provide an unlimited number of graphics printed on absorbent articles. There is also a need for a printing method for a component material of absorbent articles that can provide an unlimited number of graphics printed on the component material in one package. There is further a need for a packing method of absorbent articles having an unlimited number of graphics printed thereon in one package.

SUMMARY

In one aspect, the invention is directed to an absorbent product. The absorbent product includes a package and at least n absorbent articles contained in the package (n is greater than 10). Each of the absorbent articles has a body contacting surface and a garment contacting surface opposing the body contacting surface. Each of the absorbent articles includes a component material disposed between the body contacting surface and the garment contacting surface. The component material has a printed graphic which is seen through either the body contacting surface or the garment contacting surface. The n graphics of the n absorbent articles are different from each other, and preferably have a predetermined association.

In another aspect, the invention is directed to a method of printing a graphic on a which will become a component material for absorbent articles. The method includes the steps of: (a) storing graphic data in a graphic memory for printing n graphics, n being greater than 2; (b) selecting graphic data stored in the graphic memory; (c) printing a graphic based on the selected graphic data by an ink jet on the sheet material; and (d) repeating the steps (b) and (c) so that the n graphics are printed on the sheet material.

In an yet another aspect, the invention is directed to a method of producing an absorbent product including a package and at least n absorbent articles contained in the package (n is greater than 10). The method includes the steps of: (a) supplying a sheet material having a plurality of printing frames sequentially disposed along the machine direction (each printing frame including n graphics printed sequentially in the machine direction); (b) incorporating other component materials with the sheet material to form n absorbent articles in the machine direction (each absorbent article having a corresponding graphic of the n graphics); (c) detecting the printing frame in the sheet material; (d) transporting the absorbent articles which are within the detected printing frame; and (e) packing the transported absorbent articles into one package.

The foregoing answers the need for an absorbent product that can provide an unlimited number of graphics printed on absorbent articles. The foregoing also answers the need for a printing method for a component material of absorbent articles that can provide an unlimited number of graphics printed on the component material.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION

Figure 1:
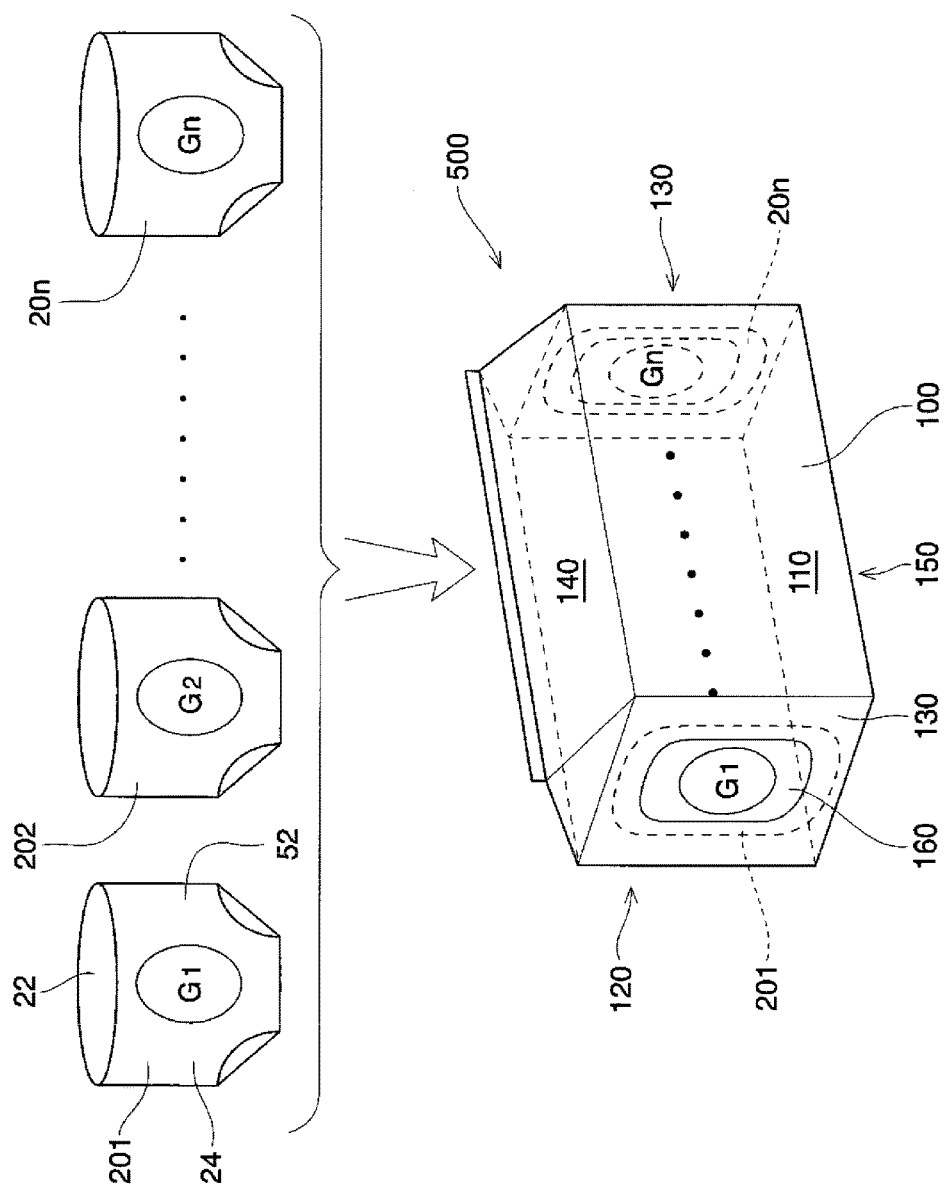
FIG. 1 is a perspective view of an absorbent product which is one preferred embodiment of the present invention.

All cited references are incorporated herein by reference in their entireties. Citation of any reference is not an admission regarding any determination as to its availability as prior art to the claimed invention.

Herein, "comprise", "include" and "contain" mean that other elements and/or other steps which do not affect the end result can be added. Each of these terms encompasses the terms "consisting of" and "consisting essentially of".

Herein, "absorbent article" refers to articles which are worn in the crotch region of a garment and absorb/contain body exudates or discharges. The absorbent article is intended to include diapers (for baby and adult) including tape type diapers, pull-on diapers and training pants; absorbent pads including sanitary napkins, pantiliners and incontinent pads; underwears, and panties for menstrual use.

Herein, "disposable" refers to articles which are intended to be discarded after a single use, composted, or otherwise disposed of in an environmentally compatible manner (That is, they are not intended to be laundered or otherwise restored or reused as an absorbent article.)

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body facing surface" refers to surfaces of absorbent articles and/or their component materials which face the body of the wearer, while "garment facing surface" refers to the opposite surfaces of the absorbent articles and/or their component materials that face away from the wearer when the absorbent articles are worn. Absorbent articles and components thereof, including the topsheet, backsheet, absorbent core, and any individual materials of their components, have a body facing surface and a garment facing surface.

Herein, "body contacting surface" refers to the surface of absorbent articles which primarily contacts the body of the wearer, while "garment contacting surface" refers to the surface of the absorbent articles that primarily contacts the wearer's garment when the absorbent articles are worn. Typically, the body contacting surface is the body facing surface of a topsheet, while the garment contacting surface is the garment facing surface of a backsheet.

Herein, "graphic" refers to images or designs that are constituted by a figure (i.e., a line(s)), a symbol or character, a color difference or transition of at least two colors, or the like. The graphic preferably has an aesthetic image or design that can provide certain benefit(s) when the absorbent article of the invention is looked or viewed by users or consumers. A variety of graphics can be used in the absorbent articles of the invention. Such graphics will be described in detail hereinafter.

A. Absorbent Product

FIG. 1 is a perspective view of an absorbent product 500 which is one preferred embodiment of the present invention. The absorbent product 500 of the invention includes a package 100 and at least n absorbent articles 201-20n which are stacked and contained in the package 100 (n is greater than 10). Each of the absorbent articles 201-20n has a body contacting surface 22 and a garment contacting surface 24 opposing the body contacting surface 22. Each of the absorbent articles 201-20n includes a plurality of component materials (e.g., a backsheet material, a topsheet material, an acquisition layer material, an absorbent core material, and a landing zone material) disposed between the body contacting surface and the garment contacting surface. The plurality of component materials constitute each absorbent article 201-20n.

Each of the component materials can be any member which constitutes at least a part of the absorbent article. At least one of the component materials is selected from the group consisting of a backsheet, a topsheet, an acquisition layer, an absorbent core, and a landing zone for waist-fastening means (not shown in FIG. 1). At least one of the component materials has a graphic(s) printed on its garment facing surface or body facing surface. (Hereinafter such a component material is referred to as "graphic component material".)

In the embodiment shown in FIG. 1, the graphic component material is a backsheet 52. The graphic component material (i.e., the backsheet 52) has a printed graphics G1-Gn which is seen through either the body contacting surface 22 or the garment contacting surface 24. (In the embodiment of FIG. 1, the graphics G1-Gn are seen at least through the garment contacting surface 24.) The graphics G1-Gn of the n absorbent articles are different from each other.

In preferred embodiments, the graphics G1-Gn are different from each other in terms of graphic design. Herein, "different in terms of graphic design" means that graphics are intended to be different when they are looked by users or consumers with their normal attentions. Thus, two graphics having a graphic difference(s) which are unintentionally caused due to a problem(s) or an error(s) in a manufacture process, for example, are not different from each other in terms of graphic design. The graphic design is determined by, for example, the color(s) used in the graphic, the sizes of the graphic (or its components), the positions of the graphic (or its components), the movements of the graphic (or its components), the geometrical shapes of the graphic (or its components), the number of colors in the graphic, the variations of the color combinations in the graphic, the number of graphics printed, the disappearance of color(s) in the graphic, and the contents of text messages in the graphic.

It should be noted that although the package 100 contains the absorbent articles 201-20n which have the graphics G1-Gn different from each other, the package 100 can further contain, if desired, one or more additional absorbent article(s) (not shown in FIG. 1) which has a graphic that is same as one the other graphics in the package 100. In other words, the absorbent product 500 of the invention includes at least n absorbent articles 201-20n which have the graphics G1-Gn different from each other, and can include an additional absorbent article(s) each having a same graphic(s).

The graphics G1-Gn can be printed on either the body facing surface or the garment facing surface of the component material. In a preferred embodiment, the graphics G1-Gn are printed on the garment facing surface of a backsheet material so that the graphics G1-Gn can be seen through the garment contacting surface 24 of the absorbent articles 201-20n, as shown in FIG. 1. In an alternative preferred embodiment, the graphics G1-Gn are printed on the body facing surface of the backsheet material so that the graphics G1-Gn can be seen through both the garment and body contacting surfaces of the absorbent articles 201-20n, e.g., the backsheet material and the topsheet material.

The backsheet preferably includes two (or more) layers of material(s). For example, the backsheet includes a laminate which includes a liquid impervious film and a nonwoven outer cover material which is joined to the garment facing surface of the liquid impervious film. The graphics G1-Gn can be printed on either the garment facing surface or the body facing surface of the liquid impervious film. Alternatively, the graphics G1-Gn can be printed on either the garment facing surface or the body facing surface of the nonwoven outer cover material. In a preferred embodiment, the graphics G1-Gn are printed on the body facing surface of the nonwoven outer cover material.

The position of the graphics G1-Gn is preferably registered within a predetermined area of the absorbent articles 201-20n such that each of the graphics G1-Gn appears on the intended position (or the predetermined area) in each absorbent articles 201-20n without unintentional variation. In the embodiment shown in FIG. 1, the graphics G1-Gn are registered in the rear region of the absorbent articles 201-20n. A preferred registration method is disclosed in U.S. Pat. No. 5,766,389 issued to Brandon et al. on Jun. 16, 1998.

The package 100 can be formed by any material and can take any structure known in the art. For example, the package 100 can be a carton which is formed by a cardboard material. In the embodiment shown in FIG. 1, the package 100 is a flexible bag which is formed by a thin film material. Such a thin film material can be made of a paper, a plastic, a recyclable material, or a laminate material comprised of two or more of these materials. In a preferred embodiment, the package 100 is a poly bag which is formed by a polyethylene film.

The package 100 includes a front panel 110, a rear panel 120 (not shown in FIG. 1) opposed to the front panel 110, side panels 130 which connects the front and rear panels 110 and 120, a top gusset panel 140 which connects the front, rear, and side panels 110, 120 and 130, and a bottom panel 150 (not shown in FIG. 1) opposed to the top panel 140.

Each of the front and rear panels 110 and 120, the side panels 130 and the bottom panels 150 are substantially planar as shown in FIG. 1. The package 100 preferably has at least one transparent window 160 which shows at least one of the graphics G1-Gn through the window 160 to get users' or consumers' attention in the market place. There is no limitation to the number of the window(s) 160 to be formed in the package 100. Preferably, in total from one to five transparent windows are formed in the front, rear, and side panels 110, 120 and 130. In the embodiment shown in FIG. 1, the side panel 130 has the transparent window 160 which shows the graphic G1 printed on the absorbent article 201.

B. Graphics

The graphics G1-Gn of the absorbent articles 201-20n preferably have a predetermined association. Herein, "association" refers to a relationship which can conceptually bond a plurality of graphics. The predetermined association is formed by the graphic designs of the n graphics. The predetermined association preferably includes a predetermined order and/or a common theme.

In a preferred embodiment, the predetermined association includes a predetermined order, and the n absorbent articles are stacked in the package in accordance with the predetermined order. The predetermined order preferably includes an order illustrating story, an order for daily activity, an order for educational training, a sequential indication means, an order of usage instruction, an order illustrating child care tips, and an order of sales promotion. More specifically, each absorbent article carries one step (or stage) in a predetermined order in the graphic, and the predetermined order is completed by the n graphics of the n absorbent articles.

The story preferably includes a children's story and a cartoon story such as Aesop's Fables, Doraemon cartoon, Sesame street, and the like.

The daily activity includes, for example, eating foods, wearing (or changing) a cloth, taking a bath, a toilet activity, making an object, cooking a food, sleeping, and growing a plant. For example, when changing clothes, the absorbent article 201 has a graphic G1 which shows the first step of changing clothes (e.g., taking off a pair of pajamas), the absorbent article 202 has a graphic G2 which shows the second step (e.g., taking off a used underwear), the absorbent article 203 has a graphic G3 which shows the third step (e.g., putting on a clean underwear), and the like. If desired, the daily activity is shown together with a preferred time for such activities in the graphics G1-Gn (e.g., 8:00 PM for sleeping).

The educational training preferably includes a puzzle or quiz on mathematics, characters (e.g., numbers and letters) which are decorated or undecorated, shapes of goods, combinations of colors, and a pattern recognition for intelligence development.

The sequential indication means includes a sequential symbol. Preferably, the sequential symbol indicates the number of the remaining absorbent articles in the package when the absorbent articles are consumed. Any sequential symbol including numbers (e.g., 1-60) and letters (e.g., A-Z) can be used. Such numbers and letters can also be used as an educational tool for kids when they are appropriately used by users.

The usage instruction can includes any information for users to effectively use absorbent articles.

The child care tips can includes any information for users (or care givers) to effectively take care of babies or children.

The sales promotion can includes any information for effectively advertising the absorbent articles to consumers.

In an alternative preferred embodiment, the predetermined association includes a common theme, and the n absorbent articles are stacked in the package in a randomly selected order. The common theme can be any theme which is consistently expressed in the n graphics. The common theme preferably includes cartoon characters (e.g., one Sesame street character is doing different activities such as playing, eating, taking a bath, and the like, or a plurality of different sesame street characters are doing same/different activities), transportation means (e.g., cars, trains, ship, planes, etc.), animals (e.g., dogs, cats, rabbits, etc.), fruits (e.g., bananas, oranges, apples, etc.), vegetables (e.g., carrots, pumpkins, potatoes, etc.), plants (e.g., tulips, morning glories, roses, etc.), and seasonal themes (e.g., snowmen, etc.).

C. Absorbent Article

Figure 2:
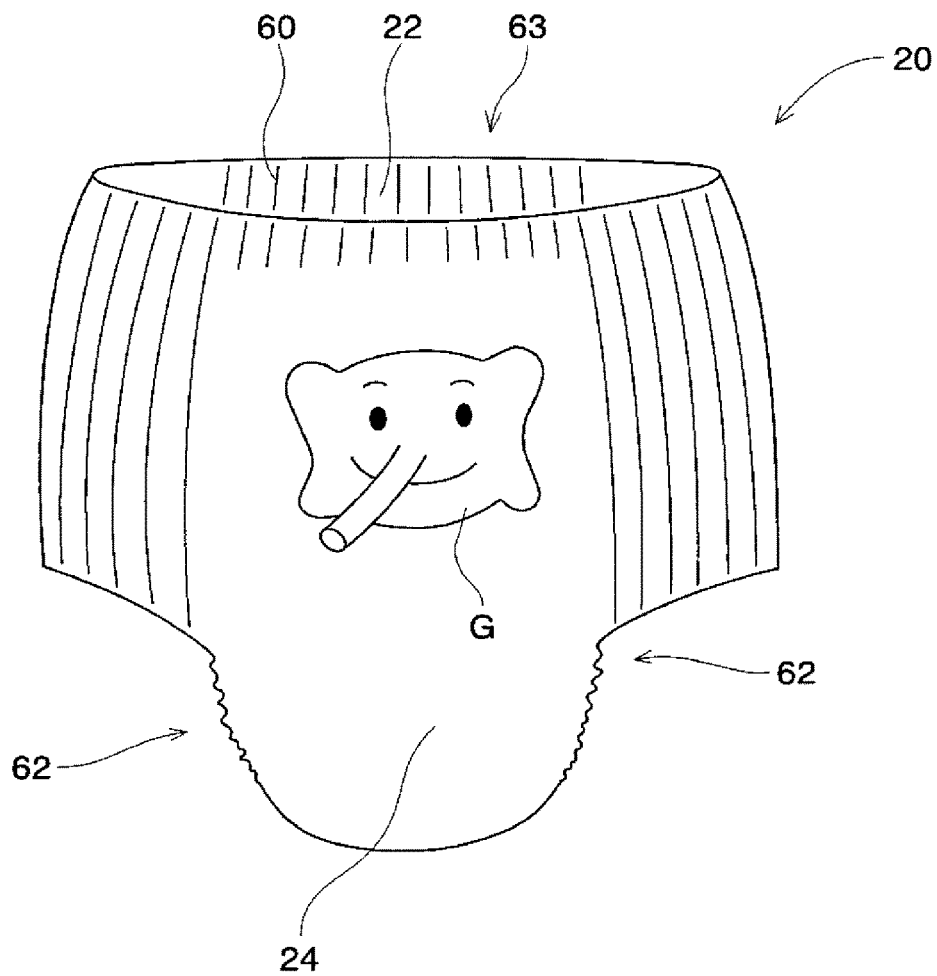
FIG. 2 is a perspective view of a pull-on diaper which is typically contained in the absorbent product shown in FIG. 1.

FIG. 2 is a perspective view of a pull-on diaper 20 (as one example of disposable absorbent articles) which is preferably contained in the package 100 shown in FIG. 1. Referring to FIG. 2, the pull-on diaper 20 has a body contacting surface 22, and a garment contacting surface 24 opposed to the body contacting surface 22. The pull-on diaper 20 shown in FIG. 2 is viewed from the garment contacting surface 24. The pull-on diaper 20 has a waist opening 63 and two leg openings 62. The pull-on diaper 20 has a graphic G which is printed in the rear region and can be seen through the garment contacting surface 24.

Figure 3:
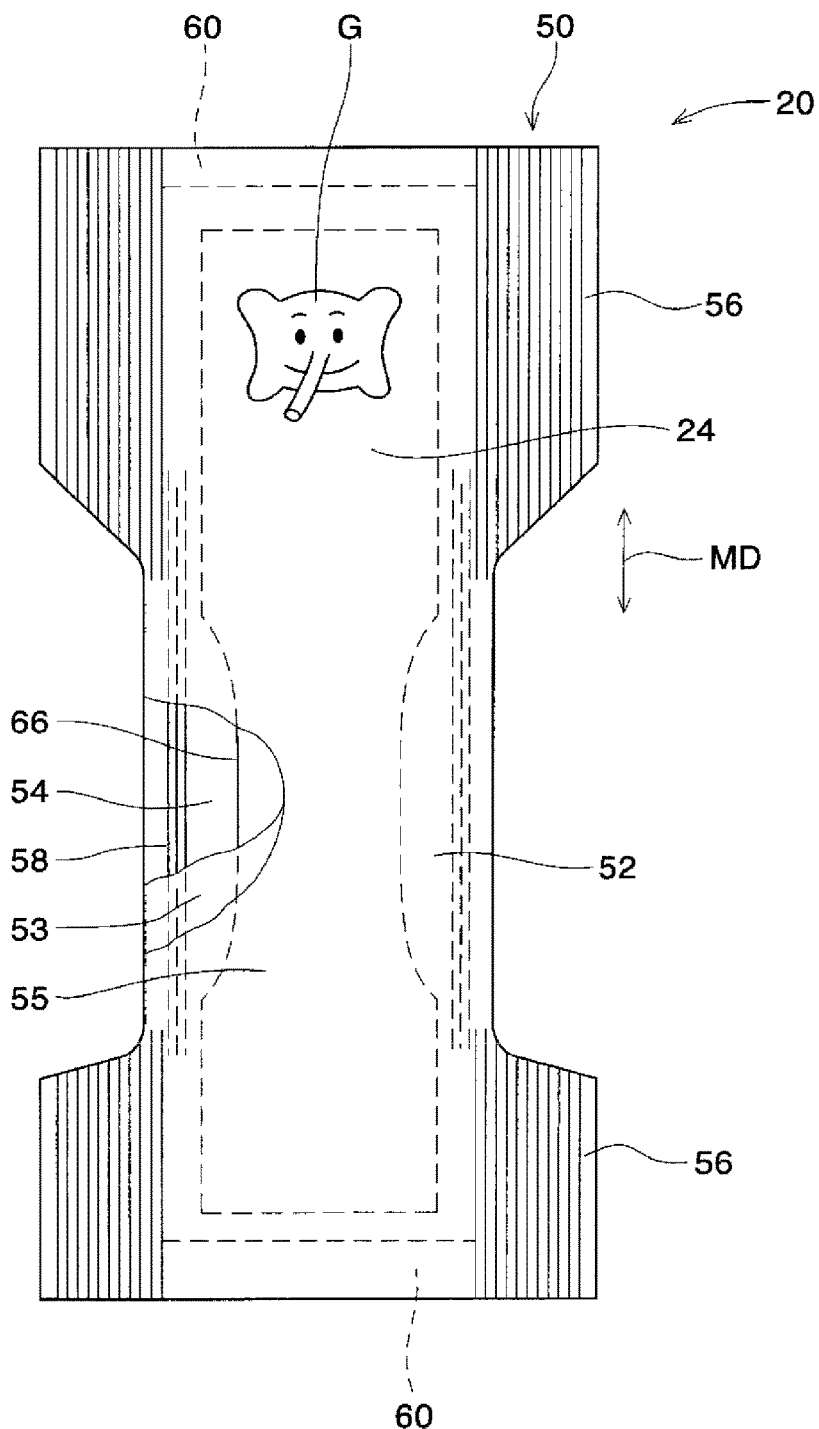
FIG. 3 is a partially cut-away plan view of the pull-on diaper of FIG. 2, which is viewed from the garment contacting surface.

FIG. 3 is a partially cut-away plan view of the pull-on diaper 20 of FIG. 2, which is viewed from the garment contacting surface 24. In FIG. 3, the pull-on diaper 20 is shown in its uncontracted state, prior to ear (or side) panels being joined together. The pull-on diaper 20 includes three primary components, i.e., a liquid pervious topsheet 54, a liquid impervious backsheet 52, and an absorbent core 66 disposed between the topsheet 30 and the backsheet 52. The outermost surface of the backsheet 52 forms the garment contacting surface 24 of the pull-on diaper 20, while the innermost surface of the topsheet 30 forms the body contacting surface 22 (not shown in FIG. 3) of the pull-on diaper 20.

The backsheet 52 can be formed by only one sheet (or layer) material such as a breathable (or microporous) film material or a non-breathable (or non-microporous) film material. Alternatively, the backsheet 52 can be formed by two (or more) sheet (or layer) materials which preferably includes a non-breathable (or breathable if desired) film material and a nonwoven outer cover material. In the preferred embodiment shown in FIG. 3, the backsheet 52 is formed by a laminate of two sheet (or layer) materials joined together, i.e., the backsheet 52 includes a non-breathable film material 53 and a nonwoven material 55 which is joined to the garment surface of the film material 53 to provide a cloth-like and/or garment-like feel.

The graphic G can be printed on any surface of the component material(s) of the backsheet 52. Specifically, the graphic G can be printed on any of the garment facing surfaces and the body facing surfaces of the film material 53 and the nonwoven material 55. Preferably, the graphic G is printed on the garment facing surface of the film material 53. This is preferred because the graphic G can be covered (or protected) by the nonwoven material 55. The graphic G can be seen through the nonwoven material 55.

The nonwoven material 55 is joined with at least a portion of the garment facing surface of the film material 53 to form a laminate structure. The nonwoven sheet 55 preferably covers all or substantially all of the garment facing surface of the film material 53 to provide the diaper with a cloth-like look and feel, although it can cover only a discrete predetermined portion(s) if desired.

The microporous film material 53 may comprise any known material being moisture pervious and liquid impervious. For example, the microporous film material 53 may comprise a breathable microporous film composed of a thermoplastic resin and inorganic fillers dispersed in the thermoplastic resin. Suitable thermoplastic polymers include polyolefins such as polyethylenes, including liner low density polyethylene (LLDPE), low density polyethylene (LDPE), ultra low density polyethylene (ULDPE), high density polyethylene (HDPE), or polypropylene and blends thereof with the above and other materials. A preferred microporous film material is a breathable microporous film material of 100% polyethyelene (25 gsm), which is available from Mitsui Chemical, Nagoya, Japan, under Code No. Espoir-N-PG-P3.

The nonwoven material 55 may comprise natural fibers (e.g. cotton or wood fibers), or may comprise fibers of polyolefins such as polyethylene and polypropylene, polyester, or any combination of such fibers. Polyolefin fibers are preferable. Further, the nonwoven may be carded, spunbond, meltblown or air-through bonded or have any other characteristic or be manufactured in any manner known in the art. A preferred nonwoven material is a spunbonded nonwoven formed by 100% polypropylene fibers (20 gsm), which is available from Mitsui Chemical Industry, Japan, under Code No. PC-0220.

The absorbent core 66 can includes any absorbent materials known in the art. Such absorbent materials are generally compressible, conformable, non-irritating to the wearer's skin, and capable of absorbing and retaining liquids such as urine and other certain body exudates. The absorbent core 66 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The topsheet 54 is preferably compliant, soft feeling, and non-irritating to the wearer's skin. Further, the topsheet 54 is preferably liquid pervious permitting liquids (e.g., urine) to readily penetrate through its thickness. A suitable topsheet 54 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 54 can be rendered hydrophilic by treating it with a hydrophilic finishing oil or a surfactant.

The absorbent core 28 is preferably joined to the backsheet 52 and the topsheet 54 by attachment means (not shown) such as those known in the art.

The pull-on diaper 20 can include other features which are preferably used in disposable pull-on diapers known in the art. For example, the pull-on diaper 20 preferably includes elastically extensible side panels 56 to ensure a comfortable and contouring fit of the pull-on diaper 50 to the wearer. The side panels 56 are joined at seams to form the waist opening 63 and the leg openings 62. The pull-on diaper 20 preferably further includes leg elastics 58 and waist elastic region 60 to enhance the fits around the legs and waist openings 62 and 63 of the wearer. Preferred leg elastics designs as well as leg cuff designs are disclosed in, for example, U.S. Pat. No. 4,695,278 issued to Lawson on Sep. 22, 1987; and U.S. Pat. No. 4,795,454 issued to Dragoo on Jan. 3, 1989.

D. Printing Apparatus and Manufacturing Process

Figure 4:
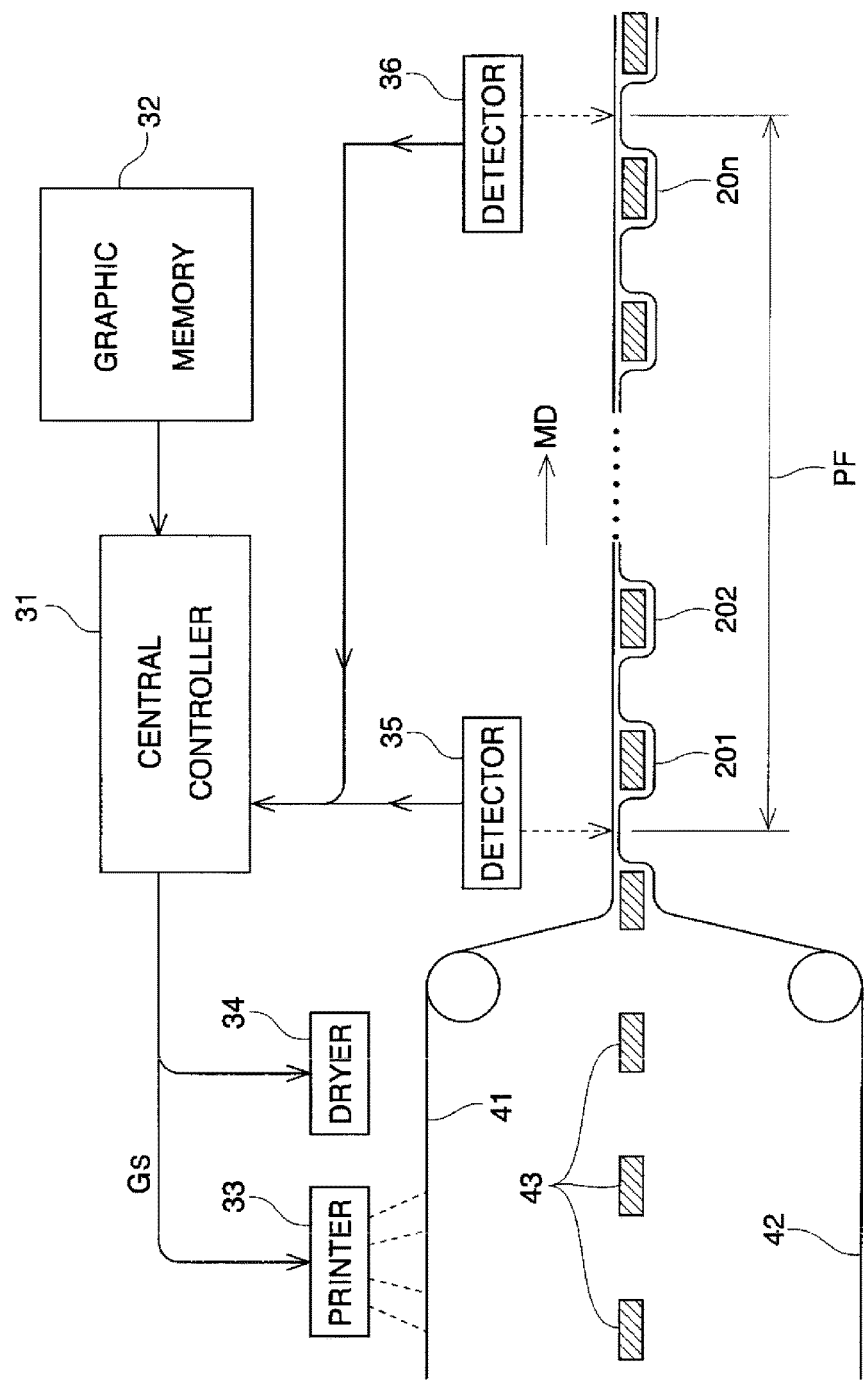
FIG. 4 is a simplified block diagram of a printing and manufacturing apparatus for disposable absorbent articles.

FIG. 4 is a simplified block diagram of a printing and manufacturing apparatus for disposable absorbent articles. Referring to FIG. 4, the printing apparatus includes a central controller 31, a graphic memory 32, a printer 33, and a dryer 34. The controller 31 controls the graphic memory 32, the printer 33, and the dryer 34 for printing graphics.

The graphic memory 32 stores necessary graphic data for the graphics G1-Gn (n is greater than 2). The controller 31 selects the graphic data stored in the graphic memory 32 and produces graphic signals Gs. The printer 34 prints the graphics G1-Gn on a sheet material (or a backsheet material) 41 based on the graphic signals Gs. The dryer 34 dries the ink printed on the sheet material 41 to fix the ink thereon.

The controller 31 is preferably constituted by a computer. Any computer known in the computer industry can be used. Preferably, a microcomputer which has an ability (or software) for image data processing is employed. A preferred controller is available from Scitex Digital Printing, Dayton, Ohio, USA, under the trade name "System Controller 220".

The graphic memory 32 is preferably constituted by a memory device. Any memory device known in the computer industry can be used. Preferably, an image memory device which has a large memory capacity is employed.

Any printer known in the printer industry which can print graphics based on graphic data stored in a memory device can be used as the printer 34. Preferred printers include Aprion DPS 65 Ink-jet printers, Indigo Webstream Digital Offset printers, and Scitex Digital Inkjet printers. Ink jet printers are preferably employed as the printer 34 since the ink jet printers are suitable for printing a variety of graphics based on graphic data supplied thereto. A typically preferred ink jet printer includes four printer heads which eject inks of four basic colors, i.e., cyan, magenta, yellow and black. Although the graphics G1-Gn can be drawn by a single color, they are preferably drawn by multi-colors using these four colors. A preferred ink jet printer is available from Scitex Digital Printing, Dayton, Ohio, USA, under the trade name "VersaMark" and "Dijit". Another preferred ink jet printer is available from Videojet Technologies, Illinois, USA, under the trade name "PrintPro". Yet another preferred ink jet printer is available from Aprion, under the trade name "Aprion DPS 65".

Any ink known in the printing industry can be used. A preferred ink is available from Scitex Digital Printers, Dayton, Ohio, USA, under the trade name "Scitex Versapure".

Any dryer known in the art can be used as the dryer 34.

In the embodiment shown in FIG. 4, a sheet material 41 is supplied from a stock roll (not shown in FIGS.) which contains the sheet material 41 wound up. Similarly, a sheet material 42 is also supplied from a stock roll (not shown in FIGS.) which contains the sheet material 42 wound up.

Figure 5:
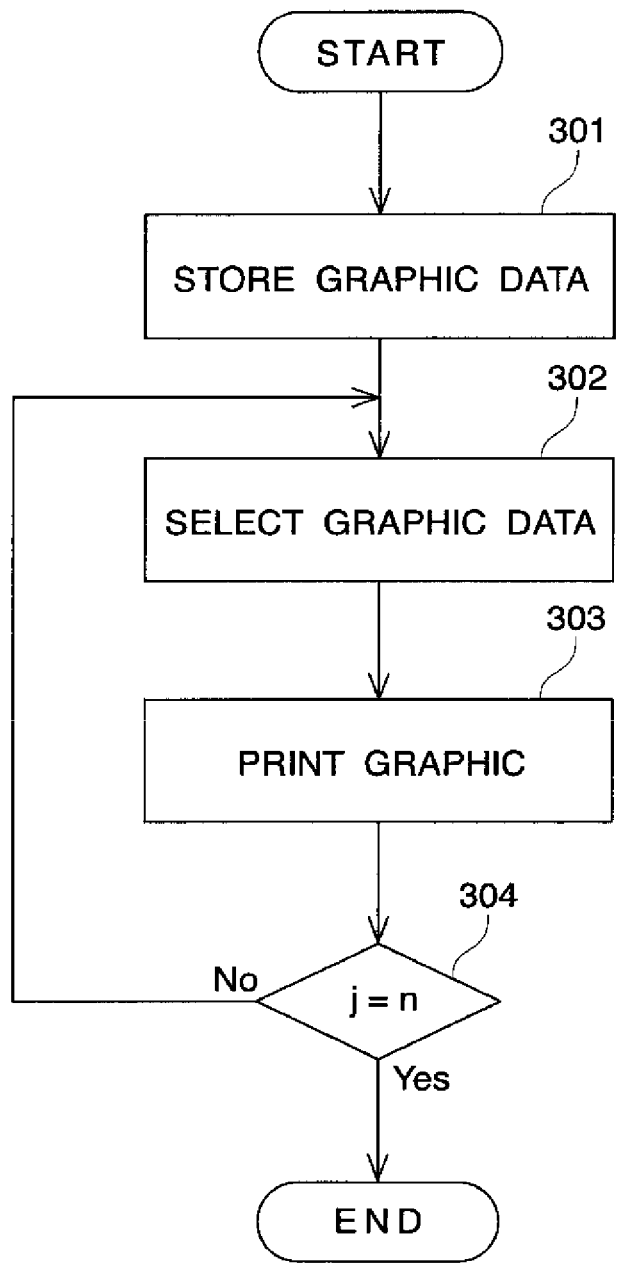
FIG. 5 is a flow chart which shows a process for printing n graphics on a sheet material.

FIG. 5 is a flow chart which shows a process for printing the graphics G1-Gn on a sheet material 41. The printing process is now explained by referring to FIGS. 4 and 5. In this embodiment, the sheet material 41 is the backsheet material. However, the sheet material can be any one of the other component materials of the absorbent article. Thus, the sheet material 41 can be selected from the group consisting of a backsheet material, a topsheet material, an acquisition layer material, an absorbent core material, and a landing zone material and/or a fastening tape material for waist-fastening means.

In Step 301, necessary graphic data for printing the graphics G1-Gn (which are different from each other) is preliminarily produced and stored in the graphic memory 32 in advance.

In Step 302, one graphic data which is used for printing the j-th graphic Gj (j: from 1 to n) is selected from the graphic memory 32. In a preferred embodiment, Step 302 includes a step of selecting graphic data stored in the graphic memory 32 in accordance with a predetermined order, as already described hereinbefore. Thus, the predetermined order preferably includes an order illustrating story, an order for daily activity, an order for educational training, a sequential indication means, an order of usage instruction, an order of how to take care of babies, and an order of sales promotion.

Alternatively, Step 302 may include a step of randomly selecting graphic data stored in the graphic memory 32.

In Step 303, the graphic Gj is printed by the printer 33 on the sheet material 41 based on the selected graphic data.

In Step 304, the number of the graphic Gj is checked, and Steps 302 and 303 are repeated so that all of the graphics G1-Gn are printed on the sheet material 41.

In a further succeeding step (not shown in FIG. 5), Steps 301-304 are preferably repeated so that the n graphics G1-Gn are periodically printed in each printing frame PF on the sheet material 41. Herein, "printing frame" is defined as a period which contains the n graphics G1-Gn. Thus, each printing frame PF contains the n graphics G1-Gn in the same order.

Although the embodiment shown in FIG. 4 is an online printing process (i.e., the printing process is a part of a diaper manufacture process), the printing process can be an offline one. In the offline printing process, it ends at a winding step for winding the printed sheet material 41 up. In a succeeding diaper manufacture process, the wound sheet member is supplied thereto.

In the embodiment shown in FIG. 4, the backsheet material 41 is joined with other component materials, i.e., a topsheet material 42 and discrete absorbent core members (or materials) 43 to produce absorbent articles 201-20n which are connected through the backsheet material 41 and the topsheet material 42. The connected absorbent articles 201-20n will be separated by a cutting equipment (not shown in FIG. 4) to produce individual absorbent articles (not shown in FIG. 4).

The apparatus further includes frame detector means which detects a printing frame PF. The frame detector means repeatedly detects printing frames PF each including n absorbent articles 201-20n. Those absorbent articles 201-20n will be packed in one common package.

In the embodiment shown in FIG. 4, two frame detectors 35 and 36 are provided. These two frame detectors 35 and 36 are preferably located along the machine direction MD with an interval (or distance) which is about equal to the total length of the n absorbent articles 201-20n in the machine direction MD. Each of the frame detectors 35 and 36 preferably includes an image sensor (not shown in FIG. 4) which detects a framing mark (not shown in FIG. 4) which is included in at least a part of the graphics G1-Gn (in one frame). Thus, the sheet material 41 has a plurality of framing marks which define the printing frames PF.

Alternatively, the frame detector means can be constituted by one frame detector (not shown in FIG. 4) which detects the framing marks. In that case, the central controller 31 monitors the number of the framing marks detected by the frame detector and identifies the printing frame PF when the number becomes n.

The framing mark can be any mark known in the art. The framing mark can be either visible or invisible as long as the frame detectors 35 and 36 can detect it. Preferably, the framing mark is printed when the graphics G1-Gn are printed on the sheet material 41, i.e., the framing mark is printed on the sheet material 41 together with the graphics G1-Gn.

The visible mark can be printed by one (or more) of the same inks which is used for printing the graphics G1-Gn. If the invisible mark is used, an invisible ink such as an ultra-violet detectable ink or a near infra-red detectable ink needs to be prepared separately from the inks for the graphics G1-Gn.

Figure 6:
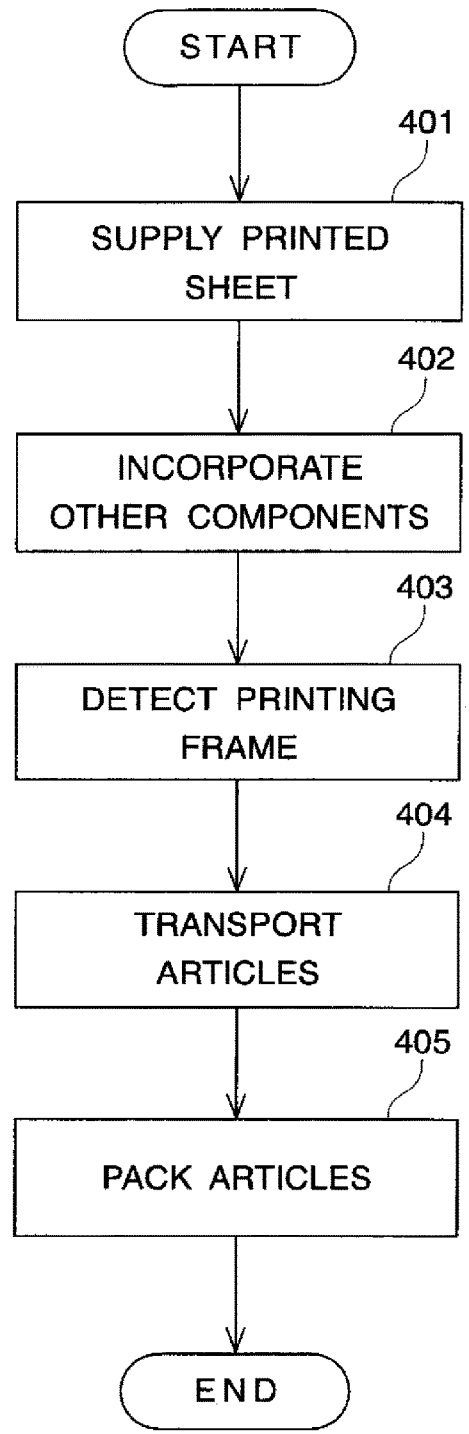
FIG. 6 is a flow chart which shows a process for packing n absorbent articles into one package.

FIG. 6 is a flow chart which shows a process for packing the n absorbent articles 201-20n into one package. The packing process is now explained by referring to FIGS. 4 and 6.

In Step 401, the sheet material 41 which has a plurality of printing frames PF sequentially disposed along the machine direction MD. Each printing frame PF includes n graphics G1-Gn printed sequentially in the machine direction MD.

In Step 402, the sheet material 41 is incorporated with other component materials 42 and 43 to form the n absorbent articles 201-20n in the machine direction MD.

In Step 403, the detecting means (e.g., the detectors 35 and 36) detects the printing frame PF in the sheet material 41. This detection is preferably performed by detecting at least one of the framing marks which have been printed in the sheet material 41.

In Step 404, the n absorbent articles 201-20n which are within the detected printing frame PF are transported to a packaging stage (not shown in FIGS.).

In Step 405, the n transported absorbent articles 201-20n are packed in one common package such as the one 500 shown in FIG. 1. After the n absorbent articles 201-20n in one printing frame are packed in the package, the process returns to Step 401 for packing the succeeding absorbent articles 201-20n in the next printing frame. (Steps 401-405 will be repeated.)

It is understood that the examples and embodiments described herein are for illustrative purpose only and that various modifications or changes will be suggested to one skilled in the art without departing from the scope of the present invention.

What is claimed is:

1. A method of making and packaging sanitary napkins, the method comprising the steps of:
   a. providing a backsheet material comprising a film having a first graphic printed thereon via an online or offline printing process;
   b. providing a topsheet material comprising an apertured formed thermoplastic film having a second graphic printed thereon via an online or offline printing process;
   c. providing an absorbent core material;
   d. combining together portions of the backsheet material, the topsheet material, and the absorbent core material to form a first sanitary napkin and a second sanitary napkin; and
   e. packing the first sanitary napkin and the second sanitary napkin into a common package;
   f. wherein step (d.) is conducted so that the first graphic associated with the first sanitary napkin and the second sanitary napkin are different from each other in terms of graphic design; and
   g. wherein step (d.) is conducted so that the second graphic associated with the first sanitary napkin and the second sanitary napkin are also different from each other in terms of graphic design.

2. The method of claim 1, wherein the first graphic is printed on the backsheet material via an offline printing process.

3. The method of claim 2, wherein the second graphic is printed on the topsheet material via an offline printing process.

4. The method of claim 1, wherein the second graphic is printed on the topsheet material via an offline printing process.

5. The method of claim 1, wherein the first graphic comprises graphic components and wherein the graphic design difference of the first graphic comprises a difference in position of the graphic components on the first sanitary napkin in comparison to position of the graphic components on the second sanitary napkin.

6. The method of claim 1, wherein the graphic design difference of the first graphic comprises variations of color combinations associated with the first graphic.

7. The method of claim 6, wherein the graphic difference of the second graphic comprises a difference in geometrical shapes on the first sanitary napkin and geometrical shapes on the second sanitary napkin.

8. The method of claim 5, wherein the graphic difference of the second graphic comprises a difference in geometrical shapes on the first sanitary napkin and geometrical shapes on the second sanitary napkin.

9. The method of claim 1, wherein the graphic difference of the second graphic comprises a difference in geometrical shapes on the first sanitary napkin and geometrical shapes on the second sanitary napkin.

10. A method of making and packaging sanitary napkins, the method comprising the steps of:
    a. providing a backsheet material comprising a film having a first graphic printed thereon via an online or offline printing process;
    b. providing a topsheet material comprising an apertured formed thermoplastic film having a second graphic printed thereon via an online printing process;
    c. providing an absorbent core material;
    d. combining together portions of the backsheet material, the topsheet material, and the absorbent core material to form a first sanitary napkin and a second sanitary napkin; and
    e. packing the first sanitary napkin and the second sanitary napkin into a common package;
    f. wherein step (d.) is conducted so that the first graphic associated with the first sanitary napkin and the second sanitary napkin are different from each other in terms of graphic design; and
    g. wherein step (d.) is conducted so that the second graphic associated with the first sanitary napkin and the second sanitary napkin are also different from each other in terms of graphic design.

11. A method of making and packaging sanitary napkins, the method comprising the steps of:
    a. providing a backsheet material comprising a film having a first graphic printed thereon;

b. providing a topsheet material comprising an apertured formed thermoplastic film having a second graphic printed thereon;
c. providing an absorbent core material;
d. combining together portions of the backsheet material, the topsheet material, and the absorbent core material to form a first sanitary napkin and a second sanitary napkin; and
e. packing the first sanitary napkin and the second sanitary napkin into a common package;
f. wherein step (d.) is conducted so that the first graphic associated with the first sanitary napkin and the second sanitary napkin are different from each other in terms of graphic design;
g. wherein step (d.) is conducted so that the second graphic associated with the first sanitary napkin and the second sanitary napkin are also different from each other in terms of graphic design; and
h. wherein one of an online printing process and an offline printing process is employed to print the first graphic and the other of the online printing process and the offline printing process is employed to print the second graphic.

* * * * *